(12) United States Patent
Ogilvie et al.

(10) Patent No.: US 8,486,146 B2
(45) Date of Patent: Jul. 16, 2013

(54) ORTHOPEDIC DEVICE ASSEMBLY WITH ELEMENTS COUPLED BY A RETAINING STRUCTURE

(75) Inventors: William F. Ogilvie, Austin, TX (US); George Makris, West Orange, NJ (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 13/466,094

(22) Filed: May 7, 2012

(65) Prior Publication Data

US 2012/0221108 A1 Aug. 30, 2012

Related U.S. Application Data

(63) Continuation of application No. 12/239,559, filed on Sep. 26, 2008, now Pat. No. 8,182,534.

(60) Provisional application No. 60/975,766, filed on Sep. 27, 2007, provisional application No. 61/050,554, filed on May 5, 2008.

(51) Int. Cl.
*A61F 2/44* (2006.01)

(52) U.S. Cl.
USPC ........................................................ 623/17.15

(58) Field of Classification Search
USPC .......................................... 623/17.11–17.16
IPC ....................................................... A61F 02/44
See application file for complete search history.

(56) References Cited

U.S. PATENT DOCUMENTS

| 5,002,576 | A  | * | 3/1991 | Fuhrmann et al. | 623/17.15 |
| 5,674,294 | A  | * | 10/1997 | Bainville et al. | 623/17.16 |
| 6,176,881 | B1 | * | 1/2001 | Schar et al. | 623/17.11 |
| 6,626,943 | B2 | * | 9/2003 | Eberlein et al. | 623/17.15 |
| 6,645,248 | B2 | * | 11/2003 | Casutt | 623/17.12 |
| 7,255,714 | B2 | * | 8/2007 | Malek | 623/17.15 |
| 7,520,900 | B2 | * | 4/2009 | Trieu | 623/17.16 |
| 7,794,501 | B2 | * | 9/2010 | Edie et al. | 623/17.12 |
| 7,905,921 | B2 | * | 3/2011 | Kim et al. | 623/17.16 |
| 2006/0190082 | A1 | * | 8/2006 | Keller et al. | 623/17.11 |
| 2006/0241767 | A1 | * | 10/2006 | Doty | 623/17.12 |
| 2007/0032873 | A1 | * | 2/2007 | Pisharodi | 623/17.12 |

* cited by examiner

*Primary Examiner* — Jan Christopher Merene
*Assistant Examiner* — Steven Cotroneo
(74) *Attorney, Agent, or Firm* — Miles & Stockbridge P.C.

(57) ABSTRACT

The present invention provides an orthopedic device assembly comprising a first assembly element, a second assembly element, and a retaining mechanism. The first assembly element has a recess that receives the second assembly element, and the retaining mechanism holds the second element in an assembled state with the first assembly element. The retaining mechanism includes a retaining member with an angular cross-section defined by a base portion and a lateral flange portion projecting from the base portion. The retaining member is inserted through an aperture of the first assembly element into a groove in a wall of the recess of the first assembly element, with the flange portion projecting laterally of the groove and overhanging a shoulder portion of the second assembly element so as to retain the second assembly element in the assembled state with the first assembly element.

19 Claims, 16 Drawing Sheets

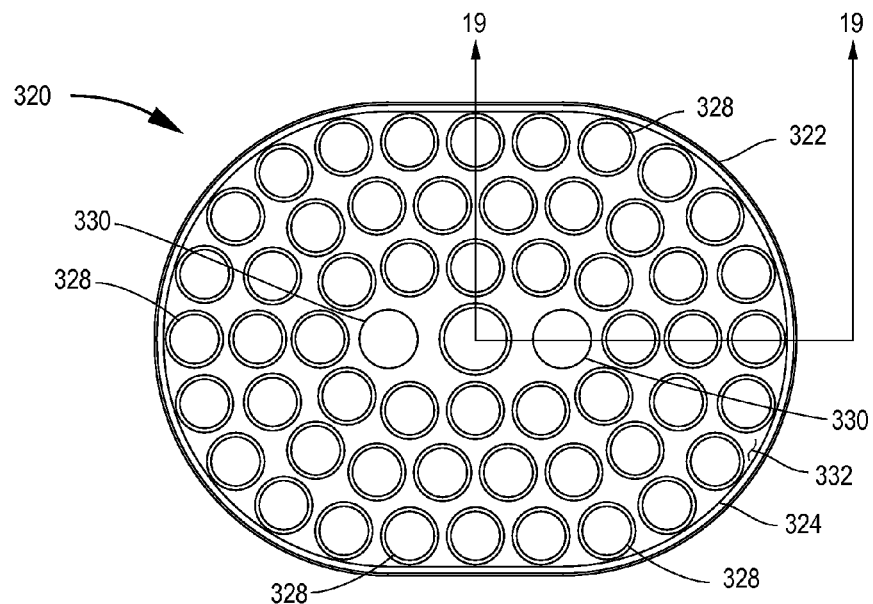
Fig. 15    Perforated plate plan (top)
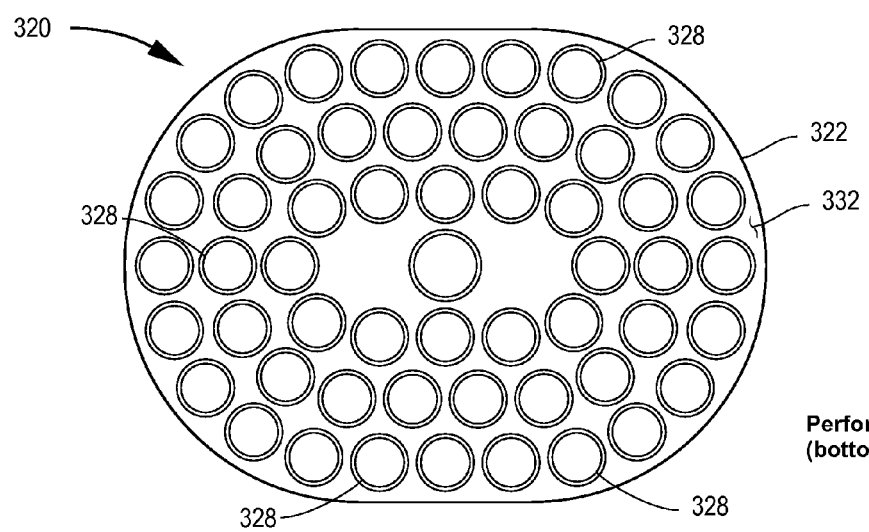
Fig. 16    Perforated plate plan (bottom)

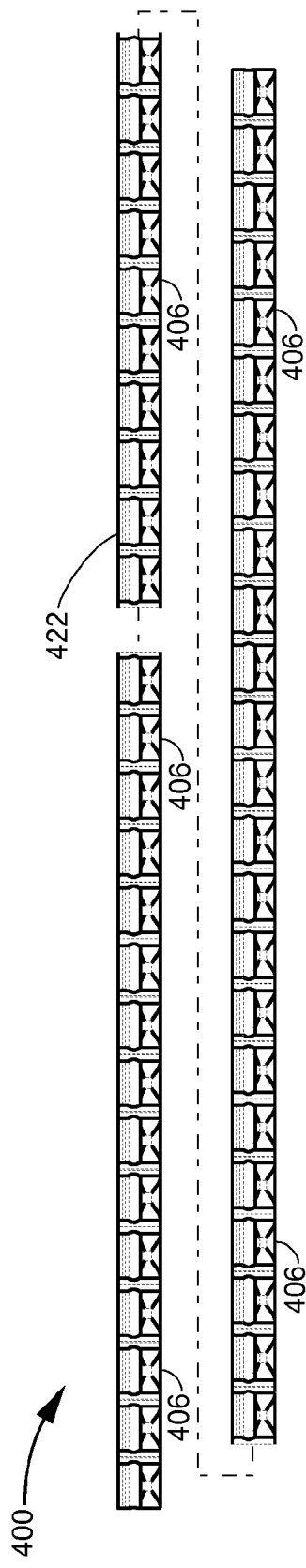
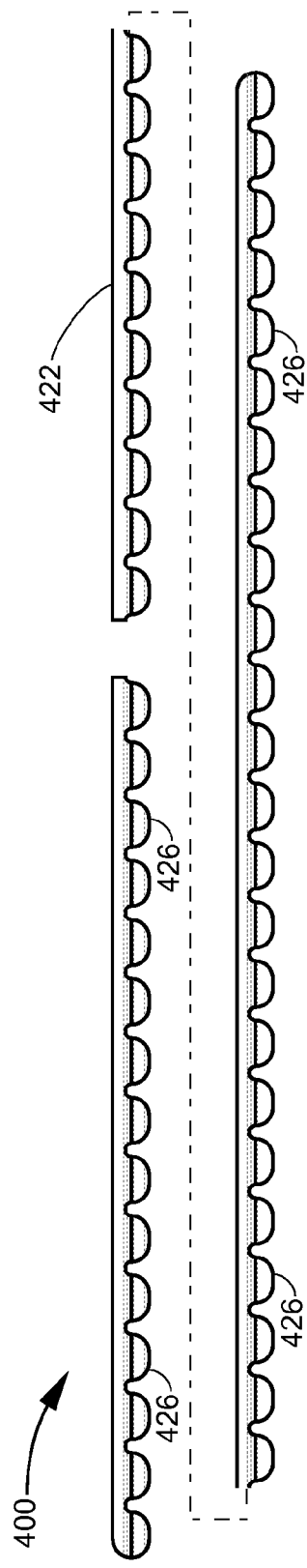
Fig. 30
Fig. 31

ORTHOPEDIC DEVICE ASSEMBLY WITH ELEMENTS COUPLED BY A RETAINING STRUCTURE

CROSS-REFERENCE TO RELATED APPLICATIONS

This application is a continuation of application Ser. No. 12/239,559 filed Sep. 26, 2008 now U.S. Pat. No. 8,182,534, which claims the benefit of U.S. Provisional Application No. 60/975,766, filed Sep. 27, 2007, the entire disclosure of which is incorporated herein by reference, and the benefit of U.S. Provisional Application No. 61/050,554, filed May 5, 2008, the entire disclosure of which is incorporated herein by reference.

BACKGROUND OF THE INVENTION

1. Field of the Invention

This invention relates to orthopedic devices having elements which are coupled by a retaining mechanism.

2. Background Art

Low back pain is a very common pathological condition, affecting approximately 80% of the general population at some time. Although most patients experience the painful symptoms only occasionally and recover fully, approximately 10% of these patients come to experience chronic and disabling low back pain in spite of various medical treatments.

The most common cause of chronic disabling low back pain is degeneration of one or more of the intervertebral discs that are positioned between the vertebrae of the spine and permit the various natural movements of the spinal column. Such degenerative disc disease (DDD) may become intractable to non-surgical treatment and have to be treated by surgical intervention. Spinal fusion has been a traditional and generally effective treatment method for chronic disabling low back pain that is not responding to non-operative treatments. More recently, alternative treatments involving replacement of the entire disc or its nucleus have been developed for treatment of discogenic pain.

The first generation of prostheses for replacement of degenerated intervertebral discs has generally incorporated mutually sliding surfaces of relatively hard materials to provide for the required intervertebral motion in flexion, extension, lateral bending and torsion. Although such prostheses have been found to be helpful, improvements in shock absorption and replication of the natural motion of the intact intervertebral disc have been sought.

Accordingly, subsequently developed prostheses have incorporated elastomeric members in order to provide for the required motion and shock absorption. Such prostheses typically include relatively hard endplates for contacting the endplates of adjacent vertebrae and fixing the prosthesis thereto, together with an elastomeric disc core, positioned between the hard endplates and attached thereto.

Attachment of the elastomeric core of such prostheses to their hard endplates has hitherto been accomplished generally by adhesives, by mechanical interlocking undercuts or the like, or by providing a porous surface on the hard endplate which engages the elastomeric core, or combinations of such techniques. For example, it has been proposed to cover the surface of the endplate that contacts the elastomeric core with a coating of small generally spherical beads bonded to that surface, e.g., by sintering or the like. The elastomeric core may then be molded against the bead-covered surface, or otherwise applied thereto, whereby the elastomer infiltrates the porous bead coating and provides a substantial mechanical interlock between the hard endplate and the elastomeric core. Such bonding surfaces are disclosed, e.g., in U.S. Pat. No. 5,071,437.

A method of attaching an elastomeric prosthesis element to a rigid portion of the prosthesis, e.g., for fastening an elastomeric core of an intervertebral prosthesis to a rigid endplate of the prosthesis, is disclosed in copending U.S. patent application Ser. No. 11/814,369, the entire disclosure of which is incorporated herein by reference. One method disclosed therein involves embedding a perforated coupling plate in an elastomeric core wherein the plate has a rim that is fastened to the wall of a coupling recess in the surface of the rigid endplate that faces the elastomeric core thereof, e.g., by an interference fit of the coupling plate rim within the coupling recess.

Nevertheless, a need has continued to exist for alternative and improved methods of securing hard elements of orthopedic devices, such as an endplate of an intervertebral disc prosthesis, to elastomeric elements such as the elastomeric core of an intervertebral disc prosthesis.

SUMMARY OF THE INVENTION

The present invention provides structures and methods which address the above-discussed need, but which are also more generally applicable to a wide range of medical and orthopedic devices as well as other devices requiring an assembly of two elements.

According to one of its general aspects, the present invention provides an orthopedic device assembly comprising a first assembly element, a second assembly element, and a retaining mechanism. The first assembly element has a recess that receives the second assembly element, and the retaining mechanism holds the second element in an assembled state with the first assembly element. The retaining mechanism includes a retaining member with an angular cross-section defined by a base portion and a lateral flange portion projecting from the base portion. The retaining member is inserted through an aperture of the first assembly element into a groove in a wall of the recess of the first assembly element, with the flange portion projecting laterally of the groove and overhanging a shoulder portion of the second assembly element so as to retain the second assembly element in the assembled state with the first assembly element.

According to one preferred implementation of the invention, an elastomeric element of a prosthesis, e.g., an elastomeric core of an intervertebral disc prosthesis, is coupled to a rigid element, e.g., a rigid endplate of the intervertebral disc prosthesis, through a rigid coupling plate, fastened to the elastomeric core, that is received within a recess in the rigid element and retained therein by a flexible retaining ring seated in a peripheral retaining groove in a wall of the recess and having projections that extend inward to confine the coupling plate within the coupling recess. The rigid element, e.g., an endplate for an intervertebral disc prosthesis, is provided with an access aperture extending from the periphery of the rigid element to the retaining groove for insertion of the flexible retaining ring. The flexible retaining ring has a generally flexible back that can generally conform to the planform of the retaining groove, and a plurality of projections having a radially extending length sufficient to extend radially inward beyond the wall of the retention recess when the retaining ring is positioned within the retaining groove.

In a particular embodiment, the coupling plate structure may be a rigid plate perforated to allow the plate to be embedded within the elastomeric core close to an upper or lower surface thereof. Alternatively, the coupling plate structure may include a suitably rigid screen element suitable for embedding within the elastomeric element and provided with a rigid rim for engagement with the coupling recess. In a further embodiment, the coupling plate structure may include a suitably rigid plate provided with an attached generally porous structure on a major surface thereof that can be impregnated with an elastomeric material to fasten the elastomeric element to the rigid coupling plate. Suitable structures for implementing the fastening of the coupling plate to the elastomeric element or core are disclosed in U.S. application Ser. No. 11/814,369, referenced above. Thus, an attached screen layer, a layer of trabecular metal or other porous metal, posts or fins upstanding from the surface and provided with lateral apertures, or the like, are suitable structures for fastening the elastomeric element of the prosthesis to the generally rigid coupling plate. Although not strictly limited in principle, the invention is most preferably applied to surgical implants, such as prostheses for replacing intervertebral discs.

According to another of its aspects, the invention provides a surgical implant comprising a rigid implant element including a coupling recess with a wall provided with a coupling groove and an elastomeric element having an attached or embedded generally rigid structure designed and configured to be received within the coupling recess, and be retained therein by a flexible retaining ring seated in the coupling groove and having projections extending inward beyond the wall of the coupling recess.

According to another of its aspects, the invention provides a surgical implant comprising a rigid implant element including a coupling recess with a wall provided with a coupling groove and an elastomeric element having an attached or embedded generally rigid structure designed and configured to be received within the coupling recess, and be retained therein by a flexible retaining ring seated in the coupling groove and having projections extending inward beyond the wall of the coupling recess, wherein the retaining ring is inserted into the retaining groove through an access aperture extending from the exterior of the rigid implant element to the retaining groove.

In another aspect the invention provides a surgical implant as described above wherein the retaining ring is comprised of a plurality of parts that can be separately inserted into the retaining groove.

In another aspect, the invention provides an endplate for an intervertebral disc prosthesis adapted to be fastened to an elastomeric core element of the prosthesis, wherein the endplate has a major surface facing the elastomeric core element having a coupling recess designed and configured to receive a coupling plate embedded in the elastomeric core element. The coupling plate is retained within the coupling recess by a flexible retaining ring, seated in a peripheral retaining groove in a wall of the coupling recess and inserted into the retaining groove through an access aperture extending from the retaining groove to an external surface of the prosthesis endplate.

In yet another of its aspects, the invention provides a method of manufacturing a surgical implant, comprising providing a rigid implant element with a coupling recess formed in a surface thereof and having a retaining groove in a wall of the groove and an access aperture extending from the exterior of the rigid implant element to the retaining groove, providing an elastomeric element having a rigid coupling structure fastened thereto or embedded therewithin and designed and configured to be received in the coupling recess of the rigid implant element, assembling the rigid implant element and the elastomeric element, and inserting a flexible retaining ring into the retaining groove through the access aperture in order to couple the elastomeric element to the rigid implant element.

In another aspect, the invention comprises a retaining element having an angular, typically L-shaped, cross-section, defined by a base portion and a flange portion projecting from the base portion. The retaining element is adapted to constrain relative axial movement between axially assembled structures. Typically, an exterior structural element is provided with a channel or recess that receives a generally complementary interior structural element along a common axis, with at least a portion of an inner surface of the exterior element in slidable contact with at least a portion of an outer surface of the interior element. One of the assembled elements, typically the exterior element, is provided with a retaining groove in the inner surface and has an access aperture through which the L-shaped retaining element can be inserted into the retaining groove.

The retaining element of angular cross-section has a base or back portion that forms one arm of the angular or L-shape and is received and confined within the retaining groove. The axial extent of the base or back portion has a first region that is confined within the retaining groove by contact with the outer wall of the interior element and a second region provided with a flange portion projecting outwardly of the groove. The flange portion engages the interior element of the assembly, e.g., by overhanging a shoulder thereof or fitting into a groove in the outer wall thereof to constrain axial movement of the interior element. The retaining element has particular utility in coupling an elastomeric core element of an intervertebral prosthesis to an endplate thereof as described below.

The foregoing and other aspects of the invention will be more fully appreciated from the detailed description which follows.

The invention will now be explained more fully with reference to the accompanying drawings which illustrate certain embodiments of the invention, and are to be considered as exemplary only and not limiting. In the following discussion, the invention will be described in detail mainly in connection with preferred implementations for intervertebral disc prostheses. Thereafter, additional applications of the invention will be addressed.

BRIEF DESCRIPTION OF THE DRAWINGS

FIG. 15 is a top plan view of a perforated rigid coupling plate to be received within the coupling recess of the endplate shown in FIG. 7.

FIG. 16 is a bottom plan view of the perforated rigid coupling plate of FIG. 15.

FIG. 30 is an elevational view of a retaining ring of the invention, showing a two-piece embodiment thereof.

FIG. 31 is a plan view of the retaining ring of FIG. 30.

DETAILED DESCRIPTION OF THE INVENTION AND PREFERRED EMBODIMENTS

Figure 1:
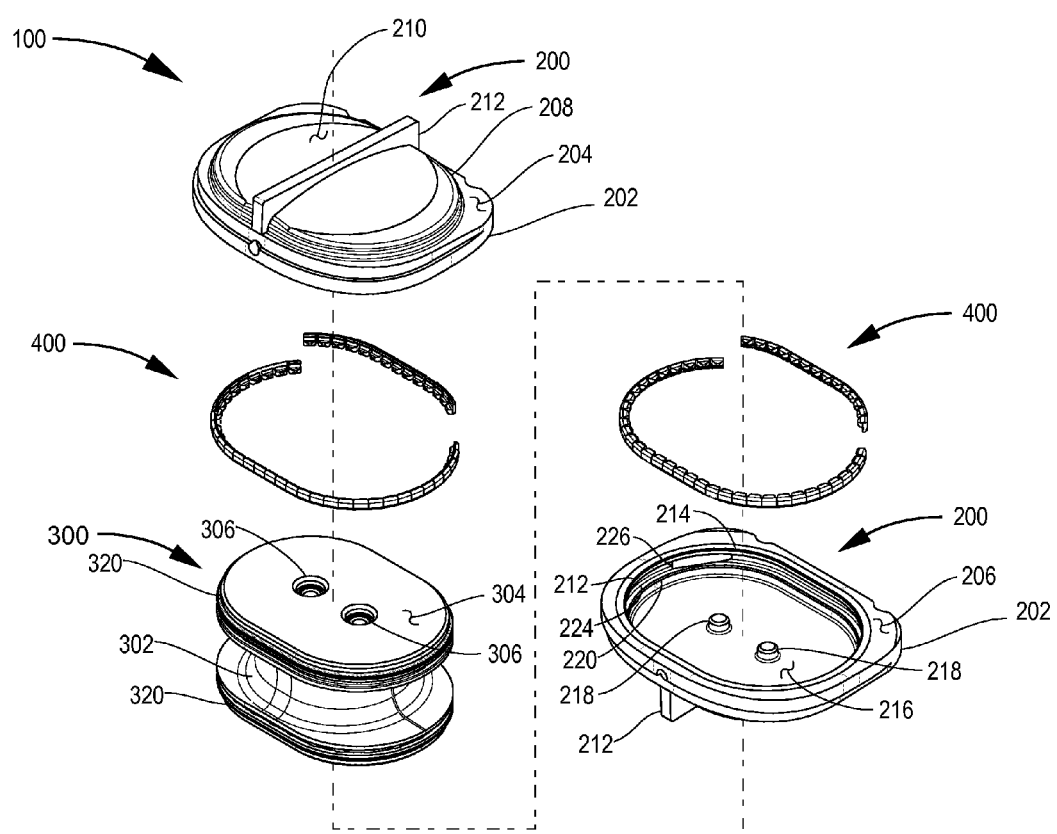
FIG. 1 is an exploded isometric assembly view of an intervertebral disc prosthesis of the invention.

When an injured, degenerated, or otherwise defective intervertebral disc has to be surgically replaced, the surgeon excises the pathological disc, or a portion thereof, and inserts in its place a prosthesis of appropriate size and shape. The cross-sectional size of the disc to be replaced, as well as the relative angle of orientation between the adjacent vertebrae, will, in general, vary, depending on the stature of an individual patient and the location within the spinal column of the intervertebral disc to be replaced. Accordingly, a variety of prostheses, having different cross-sectional sizes, with vertebra-contacting surfaces set at different angles, must be available to the surgeon in order to provide a proper fit of the prosthesis within the intervertebral space.

The invention makes it possible to construct intervertebral prostheses having a wide variation in cross-sectional size and endplate angles from a relatively small number of components. Typically, an elastomeric core element is selected that has a cross-sectional area and a general shape sufficient to support the vertical loads imposed on the prosthesis by the spinal column and allow appropriate flexural and torsional movements of adjacent vertebrae in a spinal motion segment. These elastomeric core elements may be constructed with their upper and lower end surfaces, and/or rigid coupling plates attached to the elastomeric core or embedded therein, arranged generally parallel to one another. Intervertebral prosthesis endplates are then selected that have a suitable cross-sectional area for contacting the endplates of adjacent vertebrae and have vertebra-contacting surfaces that are angled to provide matching contact with the angled end surfaces of the adjacent vertebrae. The intervertebral prosthesis endplates are coupled to the elastomeric core element to form a complete intervertebral prosthesis that can provide a functional replacement for the excised natural intervertebral disc.

The invention will be described in detail below with reference to an intervertebral disc prosthesis. However, as will be recognized by those skilled in the art, construction principles of the invention may be applied to other environments, e.g., prosthetic joints for fingers, and the like, that comprise elastomeric flexible members attached to adjacent bone surfaces through relatively rigid terminal members.

In the following description of the invention the directional terms axial, upper or superior, inferior or lower, and the like, refer to standard anatomical directions with the prosthesis considered in the orientation in which it is implanted. When used with reference to the construction of the rigid endplates of the prosthesis, the directional terms will refer to the upper endplate of the prosthesis. The practitioner will recognize that the operative structure of the lower endplate of the prosthesis is essentially identical, although, in the assembled prosthesis, the lower endplate is inverted relative to the upper endplate in order to contact the lower vertebra of a spinal motion segment.

According to one aspect the invention, an elastomeric core element has a size and shape to provide appropriate mechanical strength in a vertical direction and flexibility in antero-posterior and lateral bending and in torsion to reproduce, to the extent possible, the strength and flexibility of a natural healthy intervertebral disc.

Typically, such an elastomeric core element will have generally parallel upper and lower surfaces having a shape and dimensions suitable for fastening to rigid endplates of the prosthesis. The elastomeric core element may have an intermediate region between two end surfaces that has a reduced cross-sectional area in order to provide the elastomeric core with suitable mechanical properties.

A generally rigid coupling plate is attached to the elastomeric core at at least one, preferably both, of upper and lower surfaces of the elastomeric core. The coupling plate may be attached directly to an end surface of the elastomeric core or embedded therein relatively close to the end surface thereof. The coupling plate may have any suitable cross-sectional shape.

Typically, the coupling plate has a lateral dimension somewhat greater than its antero-posterior dimension to conform generally to the corresponding plan shape of the prosthesis endplates and the cross-sectional shape of the elastomeric core. In one embodiment, the coupling plate has generally parallel anterior and posterior edges extending longitudinally, with respective transverse ends connected by curved edges. The coupling plate has a peripheral region that extends outwardly to a peripheral edge of the elastomeric core element, or slightly beyond, by means of which the coupling plate, and the elastomeric core, are adapted to be attached to the prosthesis endplate.

A prosthesis endplate to be coupled to an elastomeric core element has a general plan shape suitable for matching the end surface of an adjacent vertebra. Such an endplate has an upper surface that is designed and configured for accurate contact with the end surface of an adjacent vertebra or with a suitably prepared recess in the end surface of the vertebra. The endplate has a lower surface intended to be positioned generally parallel to an adjacent surface of the elastomeric core element and is provided with a coupling recess or pocket to receive a coupling plate of the elastomeric core element.

The coupling recess has a cross-sectional shape generally complementary to that of the coupling plate. The coupling recess has a peripheral wall, extending between a lower surface of an endplate and a base surface of the recess. The peripheral wall of the coupling recess has an inner region, extending from the base surface of the coupling recess, having a cross-sectional shape complementary to that of the coupling plate and dimensions, antero-posterior and transverse, slightly smaller than those of the coupling plate.

The axial height of the inner region of the peripheral wall is made sufficient to allow room between the base of the coupling recess and the axial termination of the inner region of the peripheral wall for any portion of the elastomeric core element that may extend axially beyond the coupling plate. The inner region of the peripheral wall terminates at a transverse surface that provides a seat for the coupling plate when the elastomeric core element is inserted into the coupling recess.

The outer region of the peripheral wall extends to the lower surface of the endplate, and has a cross-sectional shape and dimensions, antero-posterior and transverse, greater than those of the coupling plate to permit the passage of the coupling plate into the coupling recess. Between the inner and outer regions of the peripheral wall, a retaining groove is formed therein to receive a flexible retaining ring, as described more fully below.

The retaining groove has a peripheral base, an inner wall, typically provided by a transverse terminating surface of the inner region of the peripheral wall, and an outer wall, axially spaced from the inner wall that confines the retaining ring. The endplate is provided with an access aperture extending from the retaining groove to a peripheral rim of the endplate for insertion of the retaining ring.

A prosthesis according to the invention is constructed by selecting an elastomeric core element and a pair of endplates appropriate for a particular patient and assembling them to make a complete prosthesis. A standard selection of prostheses may be manufactured and supplied to provide a stock of prostheses suitable for most patients. A complete prosthesis is prepared by inserting an end surface of an elastomeric core element into a coupling recess of a first endplate until the coupling plate is in contact with the inner wall of the retaining groove. The flexible retaining ring is then inserted through the access aperture into the retaining groove, and advanced around the groove to hold the coupling plate in contact with the inner wall of the retaining groove. The other end surface of the elastomeric core element is then inserted into the coupling recess of a second endplate and retained therein by inserting a flexible retaining ring according to the invention.

The flexible retaining ring, or lockring, has a flexible back that, when the retaining ring has been inserted, is seated generally against the base of the retaining groove. The retaining ring is provided with a plurality of projections, or teeth, relatively closely spaced along a flexible edge of the retaining ring, that extend inward beyond the outer region of the peripheral wall of the coupling recess. These projections or teeth bear against a lower surface of a peripheral rim region of the coupling plate and retain it within the coupling pocket to securely couple the elastomeric core to the rigid endplate.

The retaining ring may comprise a single flexible element or wire that is inserted through the access aperture and advanced along the retaining groove until the projections engage substantially the entire periphery of the coupling plate. Alternatively, the retaining ring may comprise two sections, one of which is pre-installed into a minor portion of the coupling groove. Thereupon, the elastomeric core element is inserted into the coupling recess by tilting the core element and a rigid coupling plate to allow the rim of the coupling plate to be inserted under the pre-installed section of the retaining ring. Then the core element is tilted back to move the entire coupling plate into the coupling pocket, and the second section of the retaining ring is inserted through the access aperture into the retaining groove to complete the coupling process. If a two-piece retaining ring is used, a shorter section is inserted through the access aperture and forced around the retaining groove.

An assembly of an elastomeric core element and two rigid prosthesis endplates thus constitutes a complete intervertebral prosthesis ready for implantation.

FIG. 1 illustrates an exploded generally isometric view of an embodiment of the invention comprising an intervertebral disc prosthesis 100, including rigid endplates 200, an elastomeric core element 300, and retaining rings 400.

Each of the endplates 200 includes a baseplate 202 having an upper surface 204 and a lower surface 206. The upper surface 204 supports a first (lower) elevated region or dome 208 and a second (upper) elevated region or dome 210. An antero-posterior fin 212 may be provided for enhanced fixation of the prosthesis to a vertebral endplate, particularly in torsion.

The lower surface of the endplate 200 is provided with a coupling recess 214. The coupling recess 214 has a base surface 216 provided with support posts 218 that engage a coupling plate 320 of the elastomeric core element 300. The coupling recess 214 has a peripheral sidewall 220 having an inner region 230 and an outer region 232 (see FIG. 10). The peripheral sidewall 220 is provided with a retaining groove 222 for receiving a retaining ring or lockring 400. The retaining groove 222 has a base surface 224, an inner wall 234, and an outer wall 236, as best seen in detail in FIG. 10.

The elastomeric core element 300 includes an elastomeric core 302, having preferably embedded rigid coupling plates 320. End surfaces of the elastomeric core element 300, as illustrated by the upper end surface 304 in FIG. 1, are provided with apertures 306 to allow the support posts 218 of the endplates 200 to engage the coupling plates 320.

Figure 2:
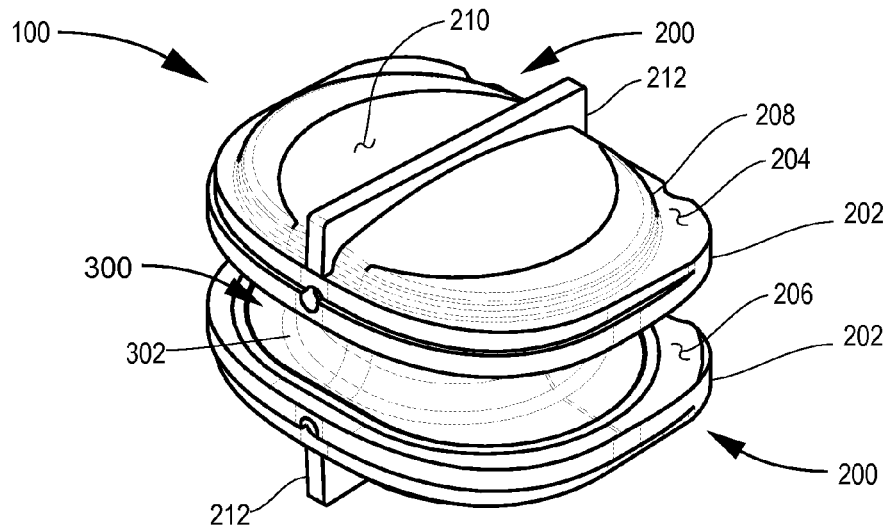
FIG. 2 is an isometric view of an assembled prosthesis of the prosthesis of FIG. 1, without a porous bone-ingrowth coating, for easier visualization of the structure thereof.

FIG. 2 is an isometric view of an assembled prosthesis 100 such as that shown in FIG. 1.

Figure 3:
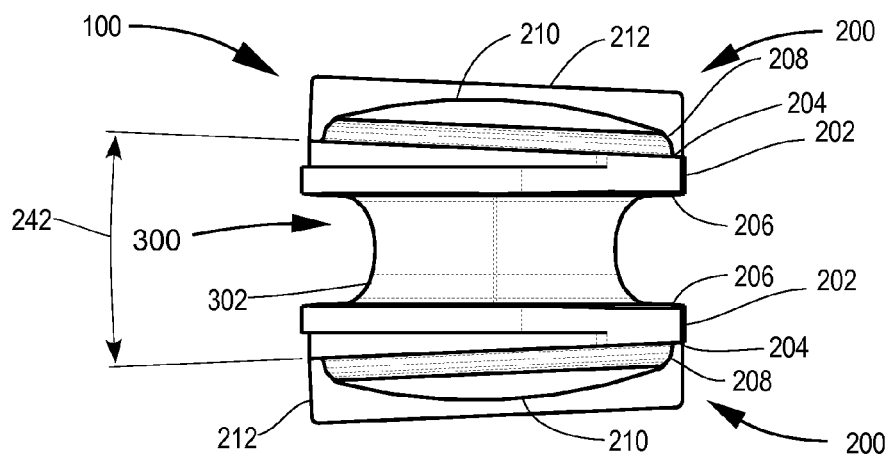
FIG. 3 is left lateral elevational view of the intervertebral disc prosthesis of FIG. 1.
Figure 4:
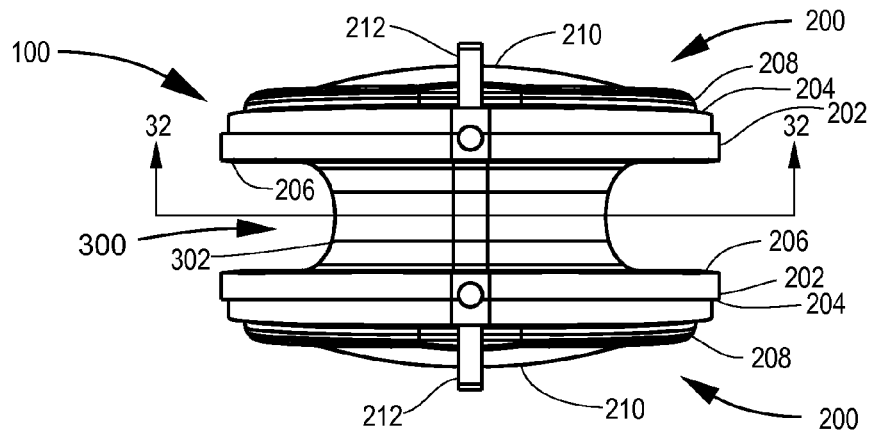
FIG. 4 is an anterior elevational view of the intervertebral disc prosthesis of FIG. 1.
Figure 5:
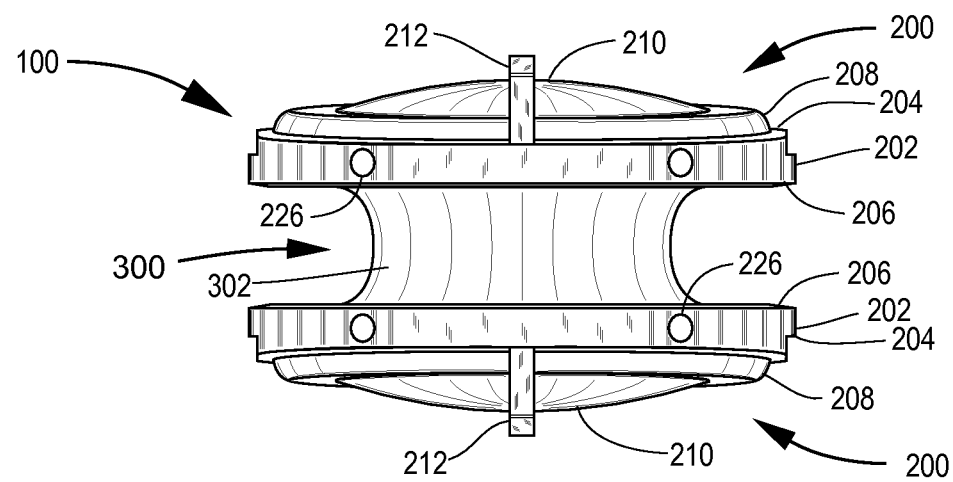
FIG. 5 is a posterior elevational view of the intervertebral disc prosthesis of FIG. 1.

FIG. 3, FIG. 4, and FIG. 5 illustrate, respectively, a lateral elevational view, an anterior elevational view, and a posterior elevational view of the assembled prosthesis of FIG. 2.

Figure 6:
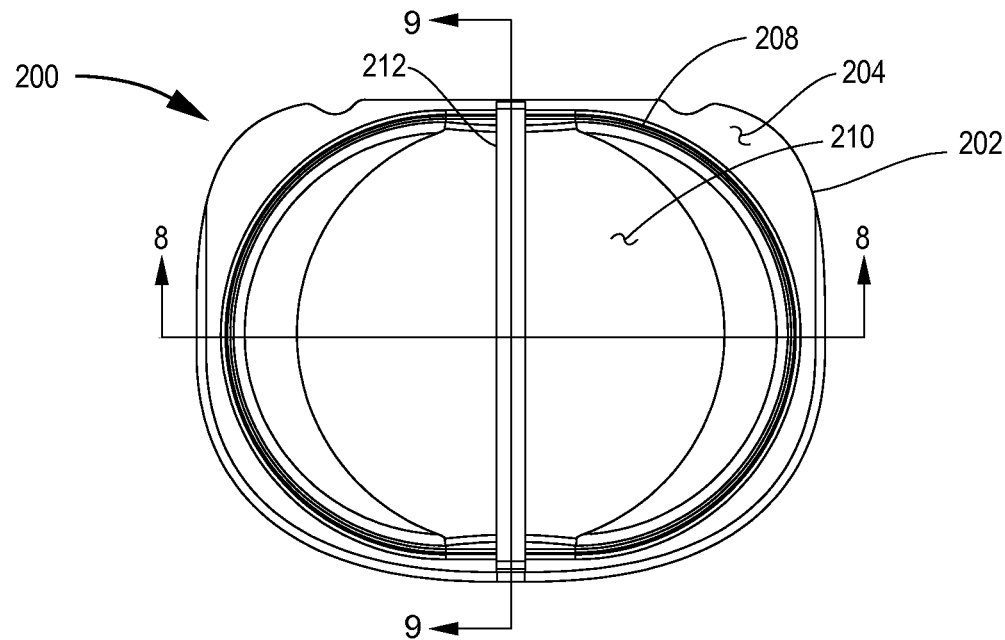
FIG. 6 is a top plan view of an endplate for an intervertebral disc prosthesis such as that shown in FIG. 1.
Figure 7:
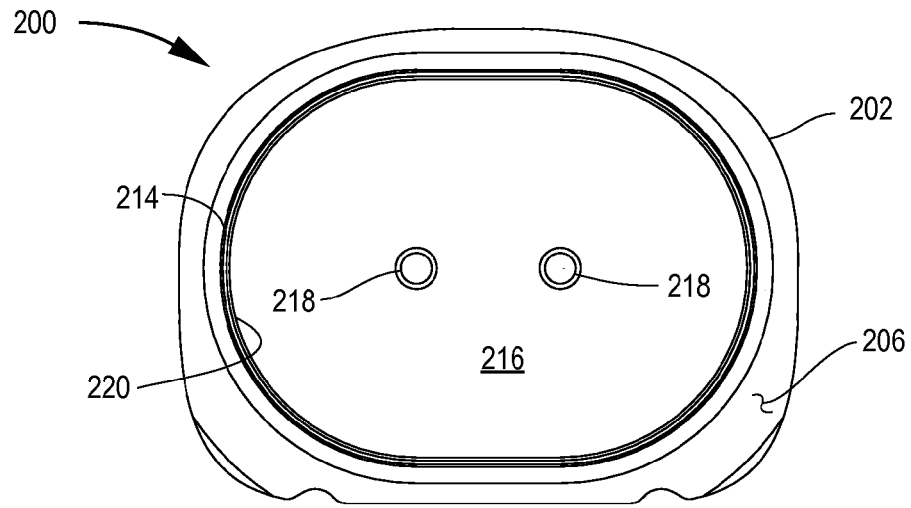
FIG. 7 is a bottom plan view of the endplate of FIG. 6.

FIGS. 6-10 illustrate an embodiment of an endplate 200 of the invention in greater detail. FIG. 6 is a plan view of the endplate 200, showing the baseplate 202, with upper surface 204, lower dome 208, upper dome 210, and fin 212. FIG. 7 is a bottom plan view of the prosthesis endplate 200, showing the baseplate 202, with lower surface 206, coupling recess 214, base surface 216 of coupling recess 214, supporting posts 218 and peripheral sidewall 220 of coupling recess 214.

Figure 8:
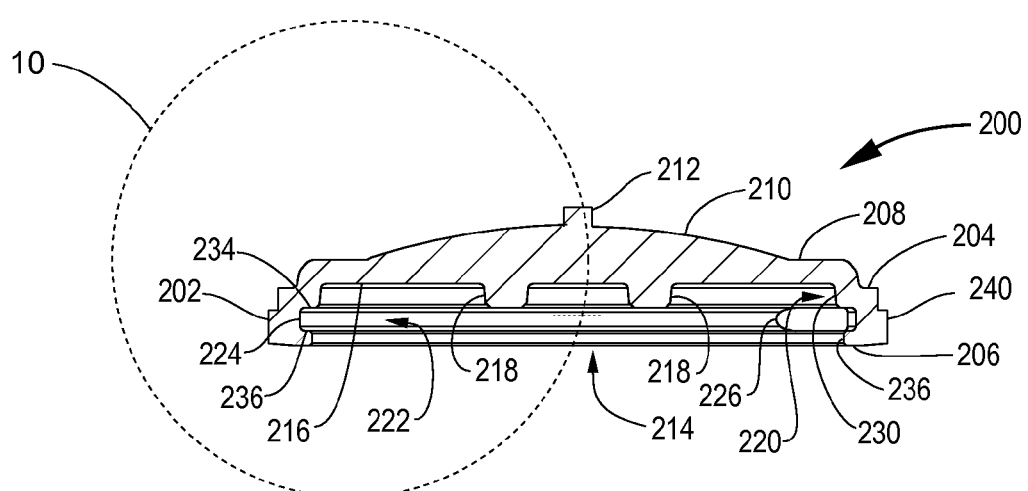
FIG. 8 is a transverse cross-sectional view of the endplate of FIG. 6, along the line 8-8 in FIG. 6.
Figure 9:
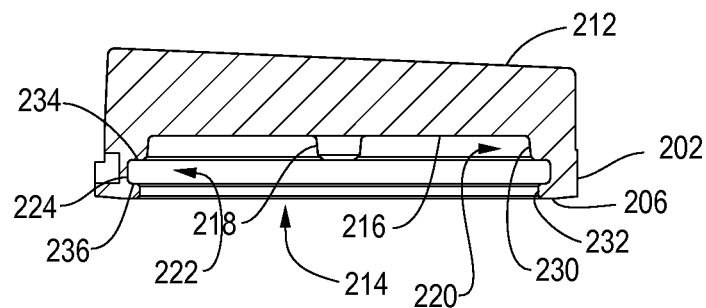
FIG. 9 is a lateral cross-sectional view of the endplate of FIG. 6, along the line 9-9 in FIG. 6.

FIG. 8 is a transverse cross-sectional view of the endplate 200, taken along the line 8-8 in FIG. 6. FIG. 9 is a median cross-sectional view of the prosthesis endplate 200 taken along the line 9-9 in FIG. 8. These figures show the baseplate 202, with the external features thereof, i.e., upper surface 204, lower surface 206, lower dome 208, upper dome 210 and fin 212. The cross-section of the coupling recess 214 of the endplate 200 includes the base surface 216 with support posts 218, and peripheral sidewall 220, with inner region 230 and outer region 232. The outer region 232 of the peripheral sidewall 220 is sized and shaped to permit insertion of the coupling plate 320 of the elastomeric core element 300 to the inner region 230 of the peripheral sidewall. The inner region 230 is sized and shaped to contact a peripheral region of the coupling plate 320 to provide a seat therefore within the coupling recess 214. The retaining groove 222 in the peripheral sidewall 220 has a base 224, an inner wall 234, and an outer wall 236, and functions to hold a retaining ring 400. An access aperture 226 for inserting the retaining ring 400 extends from the external rim 240 of the baseplate 202 to the retaining groove 222.

Figure 10:
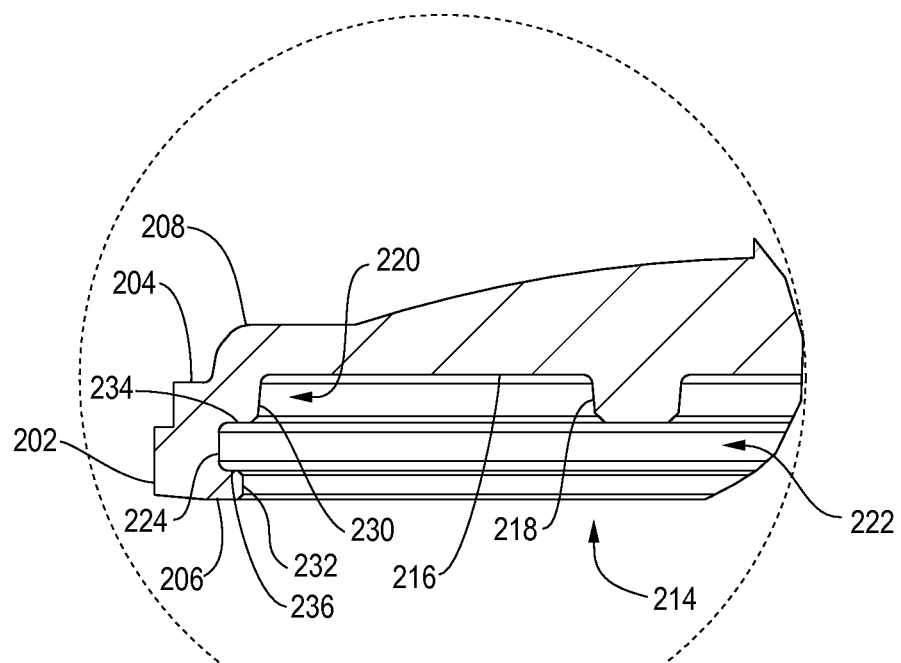
FIG. 10 is a detail cross-sectional view of a retaining groove in a wall of a coupling recess as indicated by the circle 10 in FIG. 10.

FIG. 10 is an enlarged detail cross-sectional view of the retaining groove 222 in the sidewall 220 of the coupling recess 214. It shows the sidewall 220 with its inner region 230 and outer region 232 and the retaining groove 222 with its inner wall 234 and outer wall 236.

Figure 11:
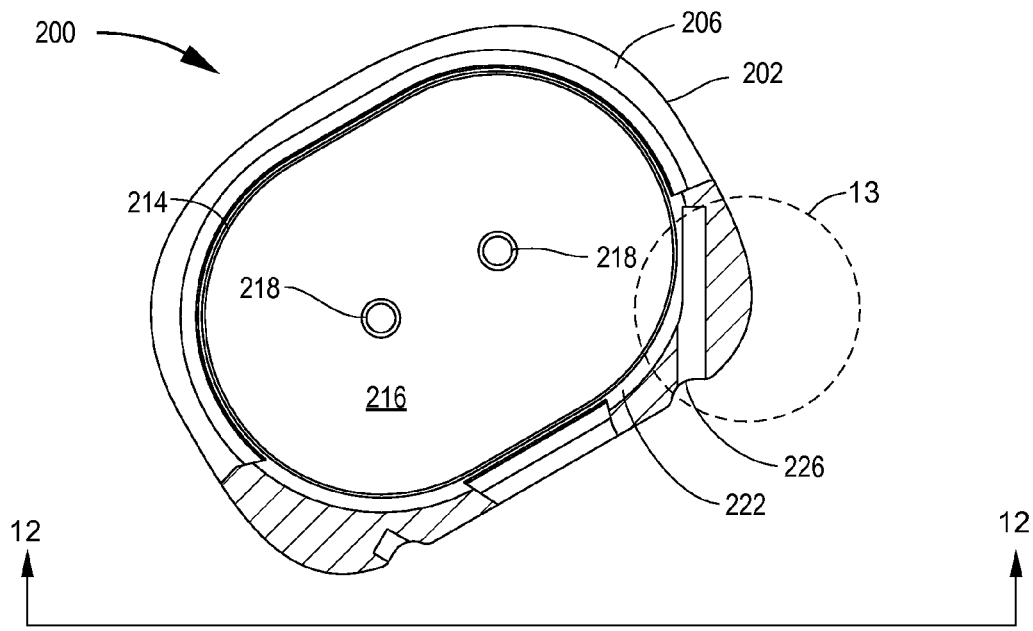
FIG. 11 is a bottom plan view of the endplate of FIG. 6, partially cut away along the line 11-11 in FIG. 12, to show an access aperture for inserting a retaining ring.
Figure 12:
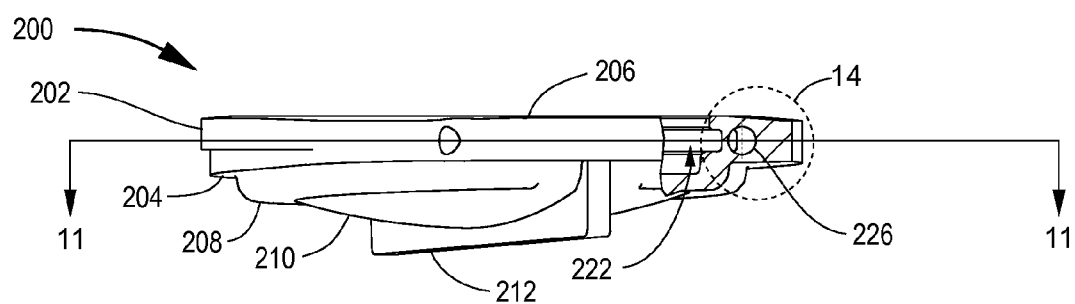
FIG. 12 is an elevational view of the endplate as shown in FIG. 11, in the direction indicated by the line 12-12 in FIG. 11, partially cut away to show the access aperture for inserting the retaining ring.
Figure 13:
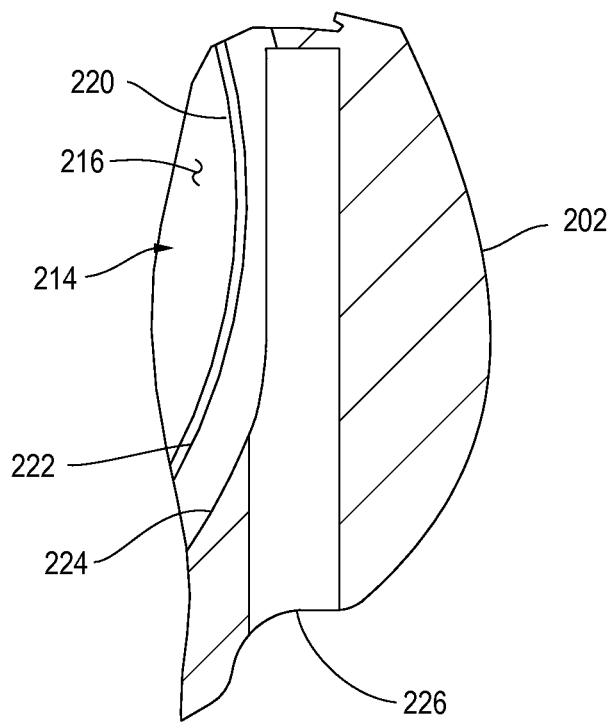
FIG. 13 is a detail plan view of the retaining ring access aperture as indicated by the circle 13 in FIG. 11.
Figure 14:
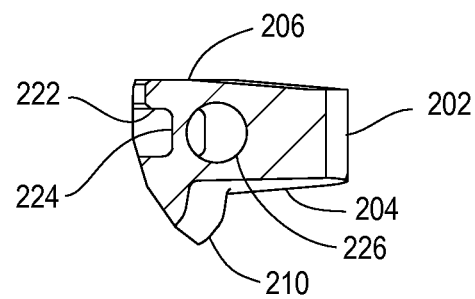
FIG. 14 is a detail elevational view of the retaining ring access aperture as indicated by the circle 14 in FIG. 12.

FIGS. 11-14 are particularly directed to the entrance aperture 226 for a retaining ring 400. FIG. 11 is a bottom plan view of the endplate 200, partially cut away along a line 11-11 in FIG. 12, to show the entrance aperture 226 to the retaining groove 222. FIG. 12 is an elevational view in the direction indicated by the line 12-12 in FIG. 11. It shows the entrance aperture 226 to the retaining groove 222. FIG. 13 is an enlarged detail plan view of the entrance aperture 226 and related structures as indicated by the circle 13 in FIG. 11. FIG. 14 is an enlarged detail elevational view of the entrance aperture 226 as indicated by the circle 14 in FIG. 12.

Figure 17:
FIG. 17 is an anterior elevational view of the rigid coupling plate of FIG. 15.
Figure 18:
FIG. 18 is a lateral elevational view of the rigid coupling plate of FIG. 15.
Figure 19:
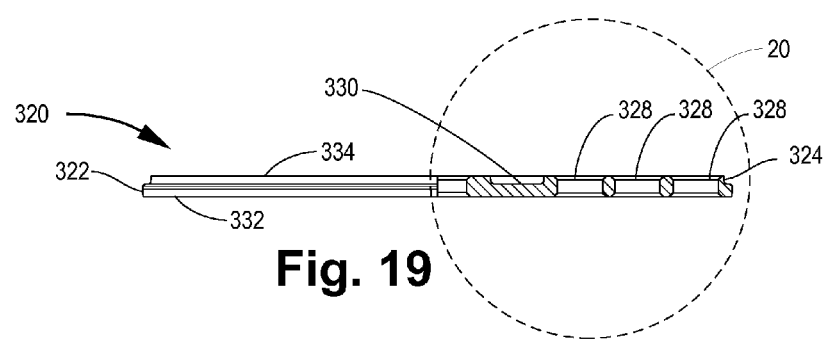
FIG. 19 is an anterior elevational view of the perforated rigid coupling plate of FIG. 15, in partial cross-section, as indicated by the line 19-19 in FIG. 15.
Figure 20:
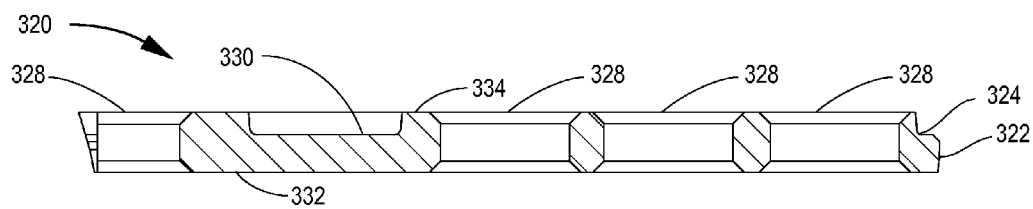
FIG. 20 is a detail of the partial cross-section shown in FIG. 19 as indicated by the circle 20 in FIG. 19.

FIGS. 15-20 illustrate a rigid coupling plate that is preferably embedded in the elastomeric core 302 in the illustrated embodiment of the invention. FIG. 15 is a top plan view of the coupling plate 320, and FIG. 16 is a bottom plan view thereof. The coupling plate 320 has upper surface 334 and lower surface 332. Coupling plate 320 has a peripheral rim 322 that is generally complementary in shape and size to coupling recess 214 in order fit generally snugly into coupling recess 214. Peripheral rim 322 of the coupling plate 320 is provided with a shoulder or notch 324 (best seen in FIG. 19 and FIG. 20) which assures positive alignment of the coupling plate 320 with the inner wall 324 of the retaining groove 224. The coupling plate 320 has multiple perforations 328 to provide for continuity between the elastomeric material of the elastomeric core above and below the coupling plate 320, and seats 330 to contact the support posts 218 of an endplate 200. FIG. 17 is an anterior elevational view of the coupling plate 320, and FIG. 18 is a lateral elevational view thereof. FIG. 19 is a partial anterior cross-sectional elevational view of the coupling plate 320 taken along the line 19-19 in FIG. 15. FIG. 20 is an enlarged detail cross-sectional elevational view of the portion of the coupling plate 320 indicated by the circle 20 in FIG. 19.

Figure 21:
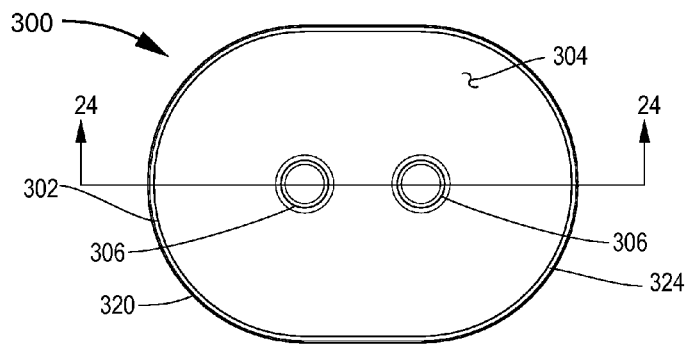
FIG. 21 is a top plan view of the core element of the intervertebral disc prosthesis of FIG. 1.
Figure 22:
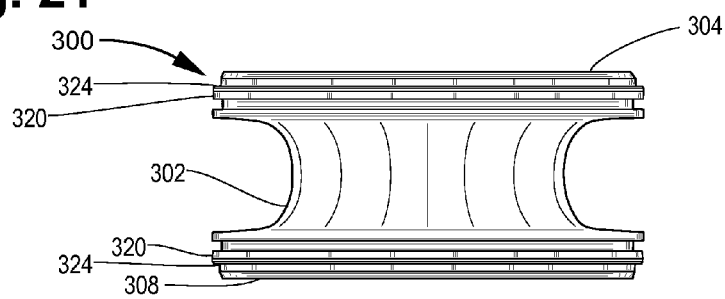
FIG. 22 is an anterior elevational view of a core element of the intervertebral disc prosthesis of FIG. 1.
Figure 23:
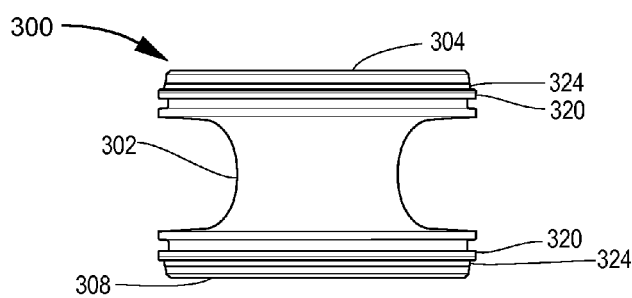
FIG. 23 is a lateral elevational view of the core element of the intervertebral disc prosthesis of FIG. 1.
Figure 24:
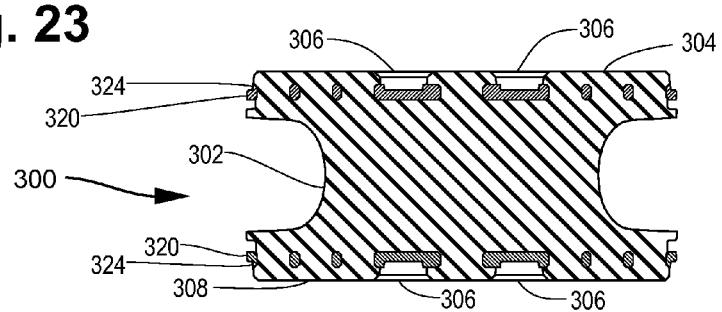
FIG. 24 is a transverse elevational cross-sectional view of the core element, taken along the line 24-24 in FIG. 21.

FIGS. 21-24 illustrate an elastomeric core element 300 of the prosthesis of the invention. FIG. 21 is a top plan view of the elastomeric core element 300 showing the top surface 304 thereof with apertures 306 therein to permit the support posts 218 of the endplate 200 to contact the coupling plate 320. FIGS. 22 and 23 are, respectively, an anterior elevational view and a lateral elevational view of the core element 300, showing coupling plates 320 embedded in the elastomeric core 302. FIG. 24 is a cross-sectional elevational view of the elastomeric core element 300, taken along the line 24-24 in FIG. 21, showing the elastomeric core 320 with embedded coupling plates 320 and apertures 306 in top surface 304 and bottom surface 308, respectively, of the elastomeric core element.

Figure 25:
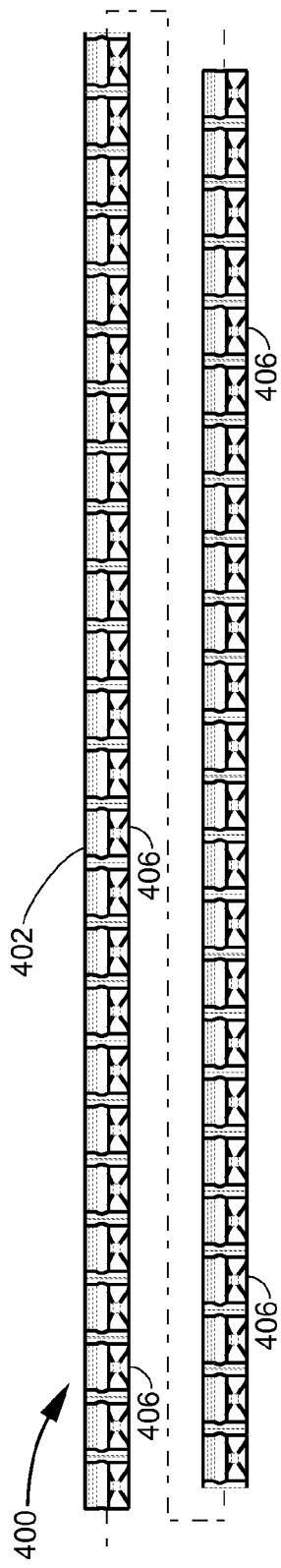
FIG. 25 is an elevational view of a retaining ring of the invention, showing a one-piece embodiment thereof.
Figure 26:
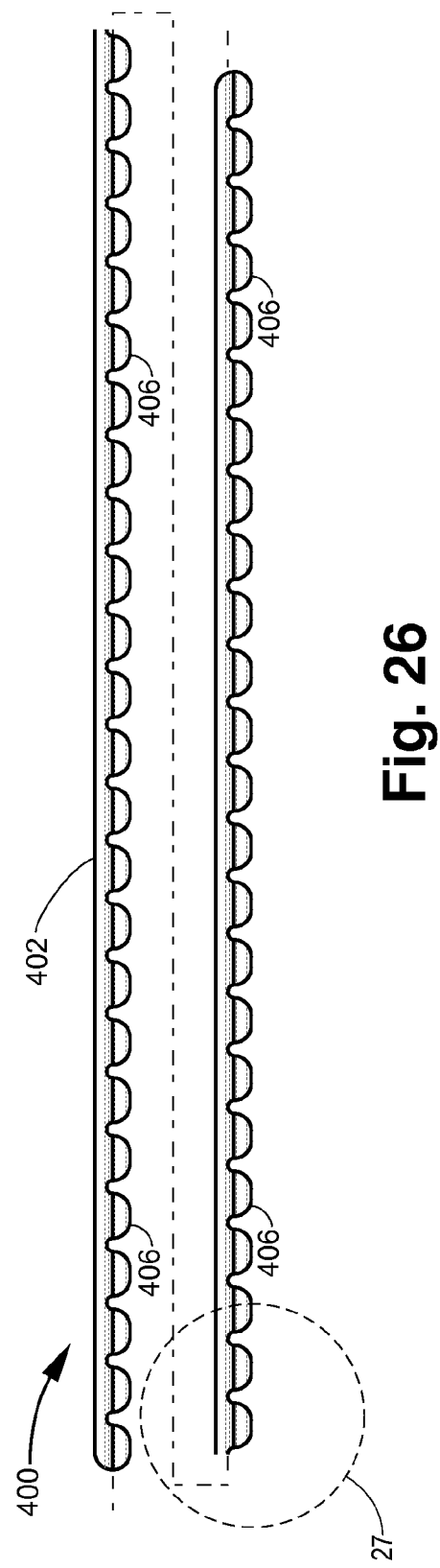
FIG. 26 is a plan view of the retaining ring of FIG. 25.
Figure 27:
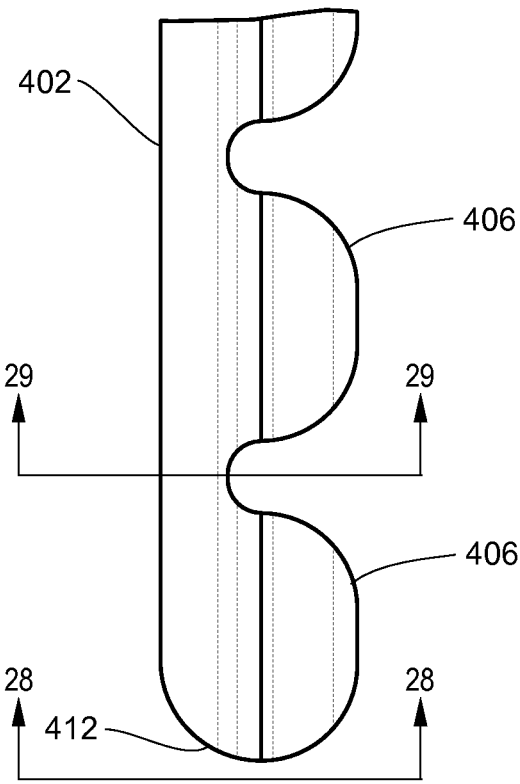
FIG. 27 is an enlarged detail of an end portion of the retaining ring of FIG. 26, as indicated by the circle 27 in FIG. 26.
Figure 28:
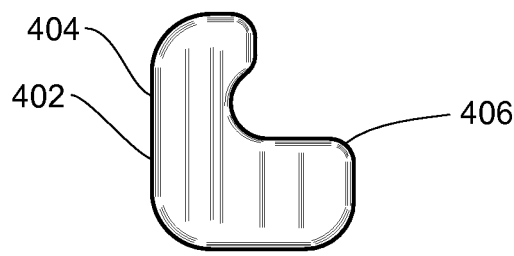
FIG. 28 is an end elevational view of the retaining ring, taken in the direction indicated by the line 28-28 in FIG. 27.
Figure 29:
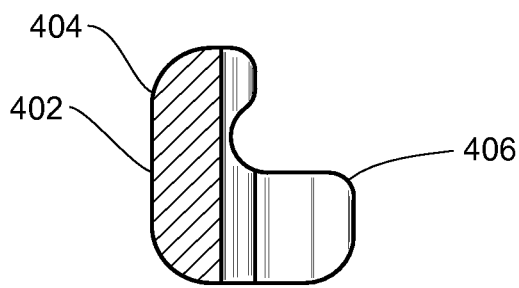
FIG. 29 is a cross sectional elevation of the retaining ring, taken along the line 29-29 in FIG. 27.

FIGS. 25-29 illustrate a retaining ring used in a prosthesis of the invention. FIG. 25 is an elevational view and FIG. 26 is a plan view of a one-piece embodiment 402 of a retaining ring 400 of the invention. The retaining ring 402 includes a back 404 and a plurality of projections or teeth 406 extending laterally to one side to give the retaining ring a generally L-shaped cross section (best seen in FIGS. 28 and 29). The gaps between the projections 406 allow the back 404 to bend in order for the retaining ring 402 to conform to the contour of a retaining groove 220 in an endplate 200. One or both of the ends of the retaining ring may be rounded as shown at 412 for convenience in inserting the retaining ring through the insertion or entrance aperture 226. FIG. 27 is an enlarged detail plan view of the retaining ring 402 as indicated by the circle 27 in FIG. 26. FIG. 28 is an end elevational view of the retaining ring shown in FIG. 27 in the direction indicated by the line 28-28 in FIG. 27, and FIG. 29 is a cross section elevational view of the retaining ring as shown in FIG. 27, taken along the line 29-29 in FIG. 27.

Figure 32:
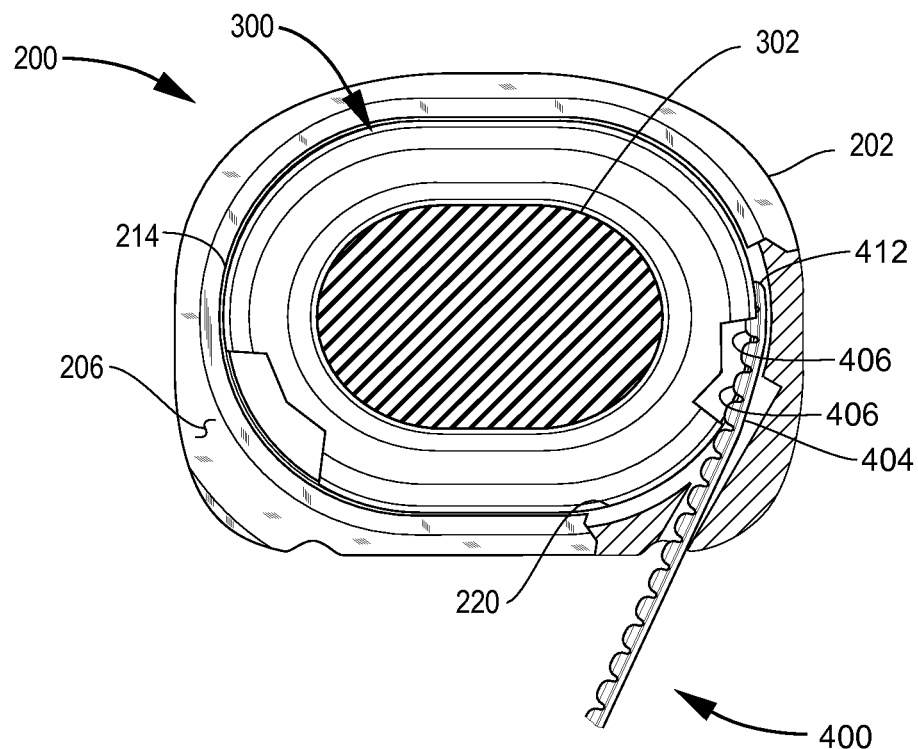
FIG. 32 is a cross-sectional view of a prosthesis assembly taken along the line 32-32 in FIG. 4, with the core element and the lower surface of the prosthesis endplate partially cut away to show the insertion of the retaining ring.
Figure 34:
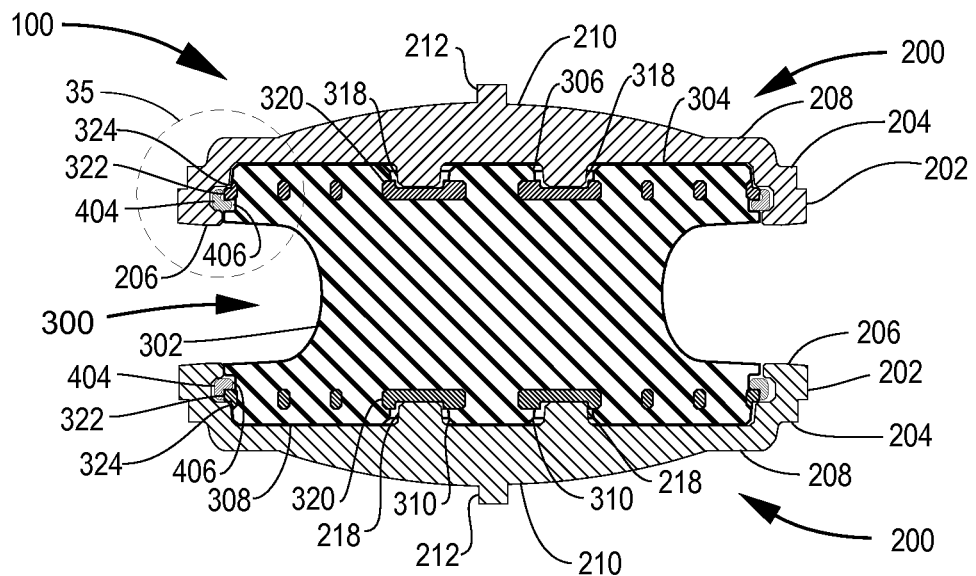
FIG. 34 is a transverse elevational cross-sectional view of an assembled prosthesis, taken along the line 8-8 in FIG. 6, but showing the entire the entire prosthesis cross section.
Figure 35:
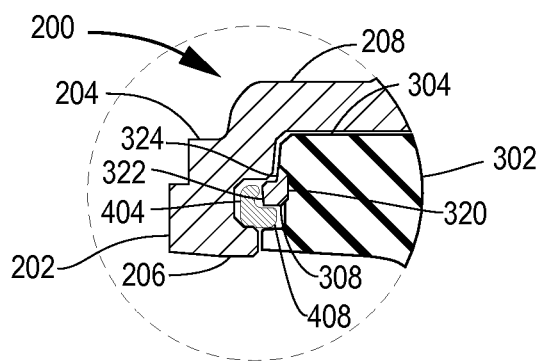
FIG. 35 is a detail of the prosthesis cross-section of FIG. 34, as indicated by the circle 35 in FIG. 34.

FIGS. 30 and 31 are an elevational view and a plan view, respectively of a two-piece embodiment 422 of the retaining ring 400. The two-piece retaining ring is similar to the one-piece embodiment 402, having a back 424 and a plurality of projections or teeth 426 extending laterally to one side FIGS. 32-35 illustrate an assembly method and an arrangement of an assembled endplate 200, elastomeric core element 300, and retaining ring 400. FIG. 32 is a cross-sectional view of an initial stage of assembly taken along the line 32-32 in FIG. 4. The prosthesis endplate 200 is shown partially cut away to show the passage of the retaining ring 400 through the entrance aperture 226. Similarly the elastomeric core element 300 is partially cut away to show the relationship between the elastomeric core element 300 and the retaining ring 400. In FIG. 32 one axial end of an elastomeric core element 300 (in cross-section) has been inserted into a coupling recess 214 in an endplate 200. When fully inserted into coupling recess 214, coupling plate 320 engages inner wall 234 of retaining groove 222 with alignment shoulder or notch 324 resting on the inner wall 234. Accordingly, alignment notch 324 of coupling plate 320 engages the inner wall 234 of the retaining groove 222 and the inner region 230 of the sidewall 220 of the coupling recess 214 (as best seen in FIGS. 34 and 35). The rounded end 412 of the retaining ring 400 has been inserted through the entrance aperture 226 and is advanced around the retaining groove 222. The projections or teeth 406 of the retaining ring 400 contact the peripheral region of the lower surface 332 of the coupling plate 320, to hold it in position within the coupling recess 214.

Figure 33:
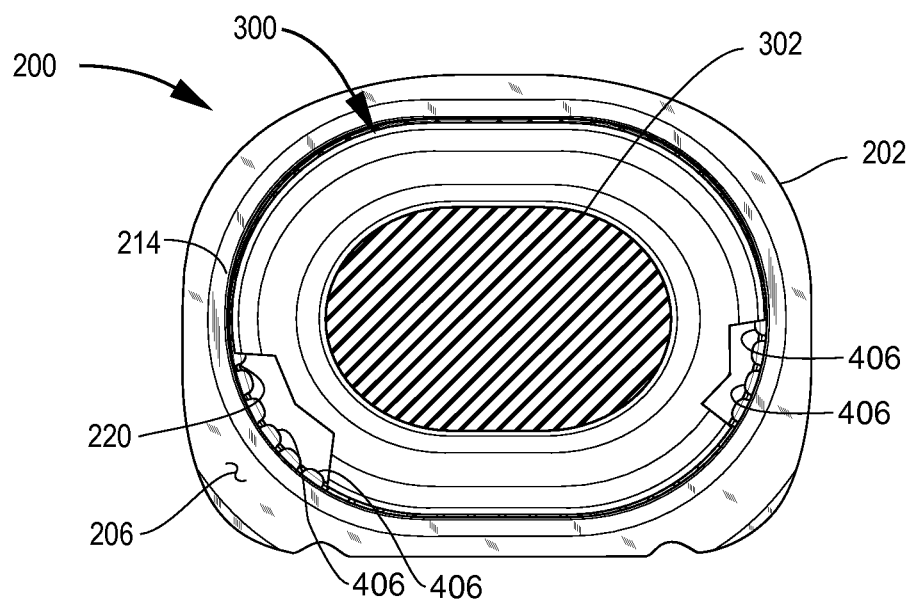
FIG. 33 is a cross sectional view of a assembled prosthesis taken along the line 32-32 in FIG. 4, with the core element partially cut away to show the inserted retaining ring.

FIG. 33 shows the retaining ring 400 fully installed, with the projections or teeth 406 holding the elastomeric core element 300 firmly coupled to an endplate 200.

FIG. 34 is an anterior elevational cross section of an assembled prosthesis taken along the line 8-8 in FIG. 6. FIG. 35 is an enlarged detail view of the region indicated by the circle 35 in FIG. 34. These figures show the relationship between endplates 200, elastomeric core element 300 and retaining rings 400. Each alignment notch 324 in the peripheral rim 322 of an embedded coupling plate 320 is seated against the inner wall 234 of a retaining groove 224. Each retaining ring 400 is seated in a retaining groove 224, with its lateral projections or teeth 406 extending beneath the rim region of a coupling plate 320 and in contact with its lower surface 332. Each coupling plate 320 and associated elastomeric core 302 are thereby firmly fixed to an endplate 200.

In the form shown (FIG. 35) the shoulder 324 is part of a member (coupling plate 320) that fits within an interior angle of the retainer 400 and is embraced between a surface of the flange 406 and an opposed surface of the groove 222.

As best seen in FIG. 35, the axial portion of retaining element 400 is firmly confined in retaining groove 224 by peripheral rim or edge 322 of coupling plate 320. This arrangement resists twisting forces imposed on retaining element 400 by axial forces tending to remove elastomeric core element 300 from coupling recess 214. At the same time, flange portion 406, extending beyond outer wall 236 of retaining groove 222 firmly restrains coupling plate 320 from axial motion out of coupling recess 214. This arrangement of coupling elements used in the prosthesis of the invention assures a firm and robust assembly of the component parts of the prosthesis, which, nevertheless, can be achieved using a retaining element that can be inserted into its retaining groove through a lateral access aperture. As will be appreciated by those skilled in the art, this mutually supporting arrangement of coupling elements can have application beyond the area of surgical prostheses, and may be generally applicable in securely coupling together axially assembled mechanical elements.

Accordingly, for example, a general application of the principles of the invention may be embodied in mechanical device, which may be a medical device or an orthopedic device, having first and second mechanical elements having first and second axes, respectively, and the elements are oriented to make the axes parallel or coaxial, wherein the elements are coupled to prevent relative axial motion in at lest one direction by a laterally inserted retainer. In such a device the first element will have a surface having a coupling region that extends along the first axis and is provided with a retaining groove, for receiving the retainer, that extends within the coupling region in a direction not parallel to the axis. The retainer has an axially extending portion and a laterally extending portion, with the axially extending portion being seated within the retaining groove and the laterally extending portion extending beyond the retaining groove. The second element has one structural portion that confines the axial portion of the retainer in the retaining groove and another structural portion that contacts the laterally extending portion of the retainer and is thereby constrained from relative axial motion with respect to the first element, at least in one direction. The device is further provided with an access aperture that extends from the retaining groove to an exterior surface of either the first element or the second element for insertion of the retaining element into the retaining groove.

By the combination of endplates 200 and elastomeric core elements 300 having different sizes and configurations, a variety of intervertebral prostheses can be provided from a relatively small number of components. In particular, endplates 200 having different angles between their lower surfaces 206, which remain generally parallel to one another in the assembled prosthesis, and their upper surfaces 204 permit a variety of prostheses having different lordotic angles to accommodate different patients. The embodiment illustrated in FIGS. 1-5 exemplifies a prosthesis incorporating a pair of endplates 200, each having an angle between its lower surface 206 and its upper surface 204 of 2.5°, producing a lordotic angle of 5°, shown as angle 242 in FIG. 3. Typically, endplates having angles between lower and upper surfaces ranging from 0° (zero) to about 7.5° are made available, in order to provide lordotic angles of 0° (zero) to about 15°.

Relatively rigid portions of an intervertebral prosthesis of the invention, i.e., the endplates and the coupling plates of the elastomeric core element, may be made of any biocompatible material having appropriate strength and rigidity. Typically they are made of a biocompatible surgical alloy based on stainless steel or titanium, such as, e.g., surgical titanium alloy Ti-6% Al-4% V. The endplates and coupling plates may be manufactured by conventional metallurgical manufacturing techniques.

An elastomeric core of an elastomeric core element of a prosthesis of the invention may be made of any biocompatible elastomeric material having appropriate strength and durometer hardness to provide sufficient axial strength to support axial spinal column loads and allow the required flexibility in motion of a spinal motion segment, i.e., antero-posterior bending, lateral bending, and torsion. Such materials are well-known to those skilled in the art and include, e.g., polycarbonate-polyurethane copolymers or blends, and the like.

From the above disclosure and discussion it will be apparent to those skilled in the art that the present invention is appropriate for any orthopedic application where two or more components are desired to be connected in a secure manner. These applications include:

1. Attachment of modular components in total joint prostheses such as hip, knee, shoulder and extremities: In total hip prostheses, femoral heads of one material are frequently attached to stems of a different material requiring a strong, secure connection. This connection may be either temporary or permanent and may be assembled either during manufacturing or intra-operatively. An additional use in total hips may be the assembly of a bearing surface into an acetabular cup. In total knees, modular components are frequently used today including tibial stems, bearing inserts, femoral augmentation spacers and femoral stems. In ankle and/or wrist prostheses, a similar use of the present invention is envisaged where modular intra-medullary extensions or space filling components are frequently used and secure fixation is important. The present invention offers advantages over existing art such as Morse tapers, threaded or snap-on mechanisms in that it allows a low-profile, high strength attachment with the potential for repeated assembly and disassembly normal to the loaded direction. This would also allow for less invasive or arthroscopic assembly or disassembly of the different components.

2. Locking mechanism for an orthopedic plate and screw combination: In both trauma and spinal devices, it is often important that bone screws are prevented from backing out from a plate since this can allow soft tissue damage and loss of fixation. Typical approaches in use today either employ secondary screws to lock the primary screw head after assembly or use a deformable washer which similarly locks the screw head in place.

The present invention allows for a secure, removable fixation of a screw head in a space efficient manner while also having utility in other spinal devices such as pedicle screw fusion systems, intervertebral fusion devices, vertebral replacement implants and interspinous spacers.

3. Elastomeric devices such as spinal discs, facet replacements, prosthetic elbows, wrists, elbows and the like: In these devices, motion occurs through the compliance of a flexible elastomeric core, and a strong, space efficient attachment of this core to the adjacent bone-fixation components of the device is often necessary. The present invention provides for a strong peripheral attachment of the core so that the core itself can be designed to withstand the demanding in-vivo loads. Traditional snap ring designs require greater peripheral cross-sections to operate effectively, requiring a reduction in the size of the elastomeric core and making disassembly extremely difficult.

Furthermore, as will be apparent to those skilled in the art, the principles disclosed and exemplified in connection with the above-described structures have general application in the technology of coupling mechanical structures. Accordingly, in structures wherein certain elements must be coupled and restrained in motion along an axis, strong and secure coupling can be achieved using laterally inserted retaining elements as taught in this specification.

Figure 36:
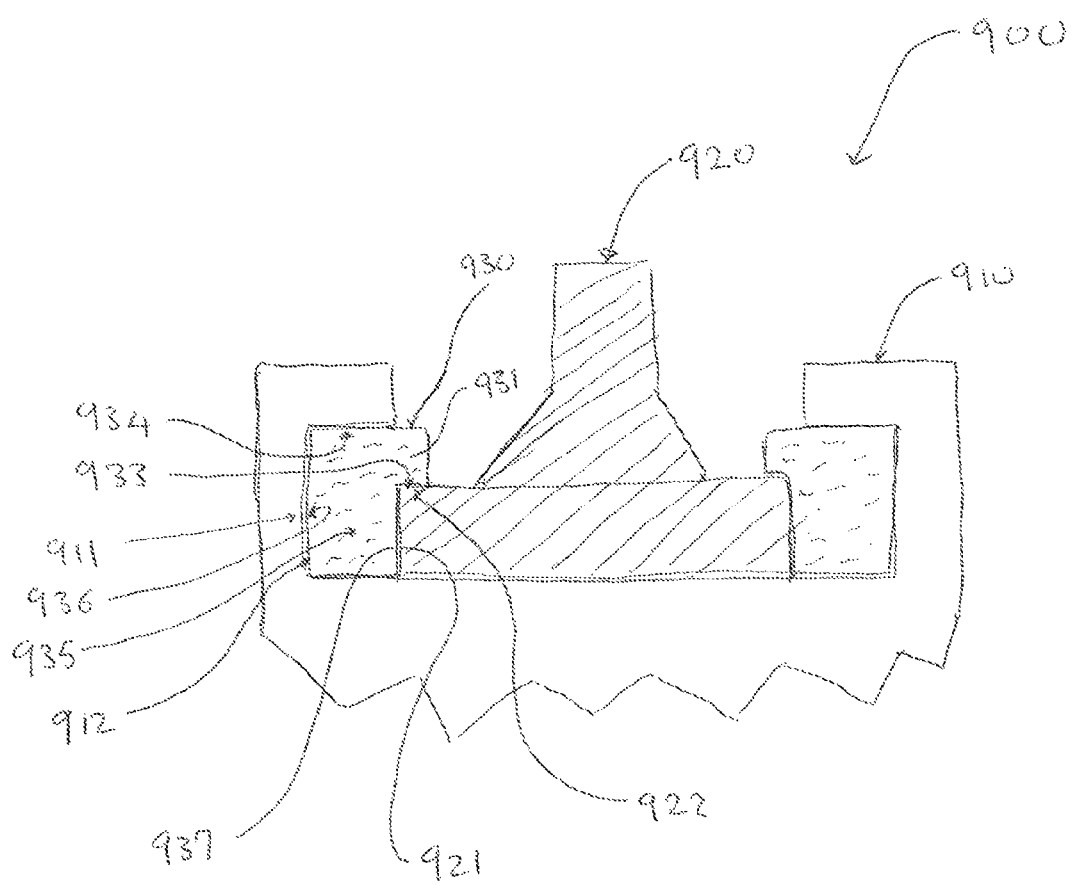
FIG. 36 is a generally schematic cross-sectional illustration of a mechanical assembly incorporating the principles of the invention.

Thus, the teachings of the present invention are well suited for application in a wide range of medical devices, orthopedic devices, and general devices having a configuration including an assembly of separately fabricated parts. A simplified illustration of such an assembly is illustrated in FIG. 36 which shows a device assembly 900 comprised of elements 910 and 920 retained from disassembly by the locking device 930. In the illustrated assembly, element 910 is provided with an axially elongated groove 911 having an elongated wall 912, and element 920 is provided with an axially elongated lateral surface 921 and a shoulder 922. Elements 910 and 920 are in axially assembled apposition, and are retained from disassembly by the locking device 930. The locking device 930 is provided with a shear segment 931 having shear surfaces 933, 934 and a retaining segment 935 having extended retaining surfaces 936 and 937. Additionally, locking device retaining segment 935 provides elongated surfaces 936 and 937 in lateral contact with the corresponding axially elongated surfaces 912 and 921 of the respective elements 910 and 920. The locking device 930 can be slidably inserted through an access aperture (not shown). The installed locking device or element 930 is therefore retained from lateral migration and presents high torsional device dislocation stiffness. Contact of opposing surfaces 933 and 922 of the respective elements 920 and 930 provides axial retention of the assembly.

Similarly, the application of the principles of the invention can be seen in the embodiments disclosed in this specification. The retaining element 400 is positioned in retaining groove 222 located in a region of sidewall 220 of coupling recess 214 between base surface 216 thereof and lower surface 206 of endplate 200. The retaining element 400 is firmly confined in retaining groove 222 by peripheral rim or edge 322 of coupling plate 320. This arrangement resists twisting forces imposed on retaining element 400 by axial forces tending to remove the elastomeric core element 300 from coupling recess 214. At the same time, flange portion 406, extending beyond outer wall 236 of retaining groove 222 firmly restrains coupling plate 320 from axial motion out of coupling recess 214. This arrangement of coupling elements used in the prosthesis of the invention assures a firm and robust assembly of the component parts of the prosthesis, which, nevertheless, can be achieved using a retaining element that can be inserted into its retaining groove through a lateral access aperture. As will be appreciated by those skilled in the art, this mutually supporting arrangement of coupling elements can have application beyond the area of surgical prostheses, and may be generally applicable in securely coupling together axially assembled mechanical elements.

The invention having been described above in terms of certain embodiments, it will be apparent to those skilled in the art that changes and alterations can be made without departing from the spirit or essential characteristics of the invention. The present disclosure is therefore to be considered as illustrative, and not restrictive, of the invention. Moreover, it will be appreciated from the above description that the invention provides a number of advantageous effects. For example, the invention generally provides for secure attachment of an elastomer to a rigid substrate. In a surgical implant, the invention provides increased fixation strength of a flexible elastomeric member to a rigid implant substrate member, such as an elastomeric core fixed to an endplate of a spinal disc prosthesis, without relying solely upon either a porous coating or an adhesive layer for attachment. The invention additionally provides a means of fixing elastomeric members to rigid members in a manner that allows for simpler manufacturing and for easier inspection of final product. Other advantages of the invention will be apparent to those skilled in the art.

We claim:

1. An intervertebral prosthesis comprising:
a core element;
a pair of end plates adapted to be disposed at opposite ends of the core element for attaching the opposite ends of the core element to respective vertebrae,
wherein at least one of the end plates has a pocket-shaped recess with an internal configuration defined by a bottom surface and a peripheral sidewall,
wherein one end of the core element is adapted to be received in the recess and has an external configuration defined by a top surface adapted to oppose the bottom surface of the recess and a peripheral side surface adapted to oppose the sidewall of the recess,
wherein the sidewall of the recess has an elongated groove that extends longitudinally around the sidewall and that is laterally open at one side towards the peripheral side surface of the one end of the core element when the one end of the core element is received in the recess;
an elongated flexible retainer adapted to be received in and along the groove,
the one end plate having an aperture for admitting the retainer longitudinally into the groove, the aperture extending to the groove laterally from an exterior point on the one end plate, and
wherein the groove and the one end of the core element have surfaces cooperable with surfaces of the retainer to restrict movement of the end of the core element relative to the one end plate.

2. The prosthesis according to claim 1,
wherein the one end of the core element has a coupling plate, and the surfaces of the one end of the core element that cooperate with surfaces of the retainer are on the coupling plate.

3. The prosthesis according to claim 1,
wherein one of the bottom surface of the recess and the top surface of the one end of the core element has protuberances and the other has openings adapted to receive respective protuberances.

4. A prosthesis according to claim 1,
wherein the retainer has an angular cross-section defined by a base portion and a flange portion projecting from the base portion, and
wherein the base portion is adapted to be received in the groove and the flange portion is adapted to project through the open side of the groove and engage a shoulder on the core element.

5. A prosthesis according to claim 4,
wherein the shoulder is adapted to fit within an interior angle of the retainer and to be embraced between a surface of the flange portion and an opposed surface of the groove.

6. A prosthesis according to claim 4,
wherein the flange portion of the retainer includes a series of flanges separated from one another by notches.

7. A prosthesis according to claim 1,
wherein the retainer is a wire.

8. A prosthesis according to claim 1,
wherein the core element includes an elastomer.

9. A prosthesis according to claim 1,
wherein the construction of the prosthesis is replicated at opposite ends thereof.

10. A prosthesis according to claim 1,
wherein the core element, the pair of end plates, and the retainer are assembled as a unit, with the one end of the core element received in the recess and held therein by the retainer received in the groove.

11. A method of making an intervertebral prosthesis that includes the steps of:
 1) providing a core element;
 2) providing a pair of end plates for attaching opposite ends of the core element to respective vertebrate,
 at least one of the end plates having a pocket-shaped recess with an internal configuration defined by a bottom surface and a peripheral sidewall,
 one end of the core element being adapted to be received in the recess and having an external configuration defined by a top surface adapted to oppose the bottom surface of the recess and a peripheral side surface adapted to oppose the sidewall of the recess,
 the sidewall of the recess having an elongated groove that extends longitudinally around the sidewall and that is laterally open toward the side surface of the one end of the core element when the one end of the core element is received in the recess;
 3) inserting the one end of the core element into the recess;
 4) providing an elongated flexible retainer adapted to be received in and along the groove,
 wherein the one end plate has an aperture for admitting the retainer longitudinally into the groove, the aperture extending to the groove laterally from an exterior point on the one end plate; and
 5) inserting the retainer into the groove,
 the groove and the one end of the core element having surfaces cooperable with surfaces of the retainer to restrict movement of the one end of the core element relative to the one end plate.

12. A method according to claim 11,
wherein the one end of the core element is provided with a coupling plate, and the surfaces of the one end of the core element that cooperate with surfaces of the retainer are on the coupling plate.

13. A method according to claim 11,
wherein one of the bottom surface of the recess and the top surface of the one end of the core element is provided with protuberances and the other is provided with openings that receive the respective protuberances.

14. A method according to claim 11,
wherein the retainer has an angular cross-section defined by a base portion and a flange portion projecting from the base portion, and
wherein the base portion is received in the groove and the flange portion projects through the open side of the groove and engages a shoulder on the core element.

15. A method according to claim 14,
wherein the shoulder fits within an interior angle of the retainer and is embraced between a surface of the flange portion and an opposed surface of the groove.

16. A method according to claim 11,
wherein the flange portion of the retainer is provided with a series of flanges separated from one another by notches.

17. A method according to claim 11,
wherein the retainer is formed as a wire.

18. A method according to claim 11,
wherein at least a portion of the core element is formed as an elastomer.

19. A method according to claim 11,
wherein the construction of the prosthesis is replicated at opposite ends thereof.

* * * * *